United States Patent [19]

Constantz et al.

[11] Patent Number: 5,279,831
[45] Date of Patent: Jan. 18, 1994

US005279831A

[54] HYDROXYAPATITE PROSTHESIS COATINGS

[75] Inventors: Brent R. Constantz, Scotts Valley; Gary C. Osaka, Mountain View, both of Calif.

[73] Assignee: Norian Corporation, Mountain View, Calif.

[21] Appl. No.: 933,877

[22] Filed: Aug. 21, 1992

Related U.S. Application Data

[62] Division of Ser. No. 504,941, Apr. 5, 1990, Pat. No. 5,164,187.

[51] Int. Cl.$^5$ .................. A61F 2/28; A61K 9/14; A61K 37/02; A61K 37/12
[52] U.S. Cl. .................. 424/423; 424/422; 424/428; 424/484; 433/212.1; 514/953; 623/16; 623/901
[58] Field of Search ............... 424/423, 422, 428, 484; 623/16, 901; 433/212.1; 514/953

[56] References Cited

U.S. PATENT DOCUMENTS 4,542,539  9/1985  Rowe, Jr. et al. .................. 623/16

Primary Examiner—Thurman K. Page
Assistant Examiner—C. Azpuru
Attorney, Agent, or Firm—Bertram I. Rowland

[57] ABSTRACT

Methods and compositions are provided for coating a substrate with a strongly adherent hydroxyapatite coating, which allows for ingrowth of natural bone and strong bonding between the coating and the substrate. The procedure provides for repetitive coatings at varying concentrations of coating forming reagents, where the highest concentration is used initially. The coating has particular application for prostheses, where porous areas of the prostheses are completely coated with a thin sturdy coating of hydroxyapatite.

12 Claims, No Drawings

HYDROXYAPATITE PROSTHESIS COATINGS

This is a division of application Ser. No. 07/504,941 filed Apr. 5, 1990 now U.S. Pat. No. 5,164,187.

INTRODUCTION

1. Technical Field

The field of this invention concerns mineralized coatings of prosthetic devices.

2. Background

The use of prosthetic devices for treatment of bone injuries/illnesses is continuously expanding with an increasingly active and aging population. The use of bone replacements for bone fractures, removal of bone, or the use of supports for weakened bone requires that the artificial bone replacement form a strong joint or bond with natural bone to insure the integrity of the structure. Bone is able to grow into adjacent structure, particularly where the adjacent structures are porous and compatible with the bone. However, not only must the bone be able to grow into a porous structure, but there must be bonding in a form which allows for a strong bond between the natural ingrown bone and the prosthetic device.

The key requirement for bony fixation of prosthetic implants is that bone grow onto and/or into the implant's surface. A number of studies have shown that calcium phosphate coatings on Co-Cr and Ti-alloy implants foster more rapid bony apposition than the bare surfaced alloys alone. Because the alternative to attaining implant fixation is cementing the implant in with PMMA, which gives immediate fixation, there is a desire to create more rapid fixation via bone apposition because during the ingrowth period there is movement between the implant and bone which leads to pain. Despite the pain, the cementless technique is used anyway because direct bony fixation is considered to be a better long term result than PMKA cements.

A number of techniques have been used to provide for a compatible surface to an otherwise incompatible but structurally acceptable prostheses. Metals have been coated with calcium phosphate ceramics by plasma spraying, ion implantation, and the like. Metal, fibers or beaded porous ingrowth surfaces have been coated by the above techniques. However, the coatings are frequently thick and brittle, have shadows where no coating has occurred, clog the pores within the porous coating and are subject to fracture. Furthermore, these techniques do not lend themselves readily to the inclusion of growth factors which may be useful in encouraging bone ingrowth and maintenance.

It would therefore be of interest to be able to develop coatings which will be compatible with bone ingrowth, provide strong bonding between the natural bone and the supporting unit and allow for binding various endogenous and exogenous factors which encourage bone growth and maintenance.

RELEVANT LITERATURE

U.S. Pat. No. 4,693,986 provides a description of the state of the art concerning apatite products as bone substitutes. Okazakai, J., et al., Biomedical Materials Research (1982), 16:851-860; Okazakai, J., et al., Caries Res. (1984), 18:499-504; and Okazakai, J., et al., J. Dent. Res. (1981), 60:845-849, described the presentation of hydroxyapatite needle-like crystals. Calcium phosphate fibers are described in a number of Japanese patents including: JP57/117621; JP53/111000; JP53/110999; JP61/201019; and JP58/054023. German Publication No. DE 33 39 996 describes calcium carbonate needles and particles. U.S. Pat. No. 3,959,192 describes calcium carbonate particle fillers. Napper and Smythe, J. Dent. Res. (1966), 45:1775-1783, describe the preparation of hydroxyapatite crystals using calcium acetate. For a review of calcium phosphate ceramics as hard tissue prostheses, see Jarcho, Clinical Orthopedics and Related Research (1981), 157:259-278. Discussion of octacalcium phosphate may be found in LeGeros et al., Scanning Electron Microscopy (1984) 4:1771-1777 and references cited therein.

SUMMARY OF THE INVENTION

Novel methods and compositions are provided relating to hydroxyapatite, particularly as coatings on a porous substrate. The method involves combining a soluble source of calcium with a soluble source of phosphate under conditions of controlled nucleation and modulated crystal growth to form a multilayered hydroxyapatite coating on a substrate. The stable substantially uniform coatings are obtained on porous structures which allow for bone ingrowth.

DESCRIPTION OF THE SPECIFIC EMBODIMENTS

Methods and compositions are provided relating to hydroxyapatite, particularly as coatings on devices which interact with bone or provide for bone ingrowth. The coatings are produced in a multistep process which provides for a strong adherent uniform thin coating of hydroxyapatite on a substrate surface, where the coating has long needles or whiskers, which appear to induce bone ingrowth and strong bonding between natural bone and the coating via bone ingrowth and opposition on a pore comprising implant.

The coatings are found to have a high $Ca_{10}(PO_4)_6(OH)_2$ surface area because of fibrous hydroxyapatite crystals $Ca10(PO_4)_6(OH)_2$. The surface area will generally range from about $1-25 m^2/cm^2$ of area. The coatings may be as thin as about 2 μm, preferably being at least about 5 μm (/μm=microns), and more preferably at least about 10 μm, and may range to 40 μm thick or greater, depending upon need. Usually, a relatively thin coating will be employed to avoid thick brittle ceramic interfaces between the substrate and the ductile bone.

The hydroxyapatite composition may be modified in a variety of ways by the introduction of other ions, as required. Other ions include fluoride, carbonate, sodium, chloride, hydrogen ions, e.g., $HPO_4$, $HCO_3$, etc., and the like. Usually fewer than about 50%, more usually fewer than about 20% of the total number of phosphate and hydroxide anions and up to 50% of calcium cation will be substituted with other ions. These substitutions will influence the in vivo dissolution behavior of the coating which may be resorbable or not resorbable.

The single crystals or whiskers which are produced by the subject method will generally range from about 0.01 microns to 20 microns in diameter and about 1 micron to 40 microns in length. The composition will usually be substantially homogeneous ($\geq 95\%$), mineralogically pure (same crystal structure), ($\geq 90\%$) and substantially homogeneous morphologically, generally varying by no more than ±20% from the average of each dimension.

The hydroxyapatite (HAP) has a net positive charge at physiologic pH which attracts charged proteins, such as collagen or other exogenous or endogenous proteins, which may serve as growth factors, chemoattractants, and the like. Thus, the coating may provide for the presence of such products on the surface of the hydroxyapatite or its analog or as part of the structure of the hydroxyapatite. The exceptionally high surface of this coating presents orders of magnitude more binding surface than the uncoated implant or the conventional calcium phosphate coatings.

The coatings may be applied to solid surfaces, porous surfaces, etched surfaces, or any other type of surface. Because the coating is applied in a liquid medium which is able to penetrate channels, pores, indentations and other structural features, a uniform coating can be obtained which can coat substantially the entire surface, without leaving exposed areas. The subject process finds particular application with devices involving fine bead layers, where the beads will be two or more layers, requiring that at least about two layers of the beads be penetrated and coated with the hydroxyapatite or its analog. Thus, penetrations are achieved in a porous substrate, such as is used in prothesis devices, of at least about 0.5 mm, more usually at least about 1 mm.

The method involves applying at least two layers, a first layer of very small crystals achieved by providing conditions which result in a high density of heterogeneous nucleation sites, so that there is a large number of hydroxyapatite nucleation sites on the substrate. This is followed by at least one additional coating under conditions which provide for a lower level of nucleation modulated crystal growth, so as to produce substantially larger crystals. Desirably, one or more additional coatings are provided, where the conditions are the same or at even lower levels of nucleation than the second coating to produce larger size crystals as compared to the second coating. Usually, there will be not more than five coatings, preferably not more than about three coatings.

The first layer will generally be of a thickness in a range of about 0.01 micron to 20 microns, with crystal size in a range of about 0.01 microns to 10 microns. The second coating will generally be of a thickness in a range of about 1 micron to 40 microns, with crystals of a size in the range length of about 0.01 microns to 20 microns. The third and successive coatings will generally range as to each layer of a thickness in a range of about 1 micron to 40 microns, preferably about 5 microns to 10 microns, having crystals of a diameter of about 0.1 to 2 microns, and a length of about 1 to 10 microns, preferably about 0.1 to 1 micron in diameter, and a length of about 2 microns to 7 microns. The total thickness of the second and succeeding layers will generally be in the range of about 5 microns to 20 microns.

The various layers can be achieved, by varying the concentration of the reactants, the pH, temperature, manner of combining the reactants in the reactor, nature of the liquid flow, and the like. Preferably, the reactants and substrate will move in relation to one another, so that the substrate is continuously encountering a specific reaction mixture. Conveniently, the reaction mixture may be streamed past the substrate, using laminar or turbulent flow, preferably turbulent flow, either by providing for a tubular reactor with a reaction mixture which may be recycled and spent ingredients replenished, or by using a mixer, where the portion of the substrate to be coated is positioned at a site displaced from the center of the reactor and the reaction mixture continuously agitated with a stream flowing around the walls or the like. The specific conditions for the reaction mixture are determined by the flow conditions determined by reactant concentration, geometry of combination, fluid flow regime, vessel geometry, and the like.

Before coating is started, the substrate may be cleaned or treated to remove any surface contaminants or promote good adhesion of the coating. Various methods for cleaning may be employed. Before the coating, the substrate may be rinsed with a degreaser, i.e., acetone, isopropanol, freon, etc. and then rinsed with an appropriate rinsing solution, e.g., deionized water. Surface treatments available are acid etchings, ion beam etchings, etc.

The reaction mixture is prepared by bringing together at an elevated temperature and at a mildly acidic to mildly basic pH, a water soluble calcium source and a water soluble phosphate source. During the addition of the calcium and phosphate sources, the pH is maintained by the addition of an appropriate acidic or alkaline medium particularly alkaline medium, e.g. ammonium hydroxide. Depending upon the particular coating involved, the solutions which supply the calcium and phosphate sources will vary in concentration, so as to vary the degree in rate of nucleation, and crystal growth modulation.

While the two reactants may be added simultaneously at an adjacent site, preferably, the calcium source will be added at a site more proximal to the substrate than the phosphate source. Thus, the calcium will be introduced into a solution in which the phosphate concentration has been replenished and these combined solutions will then directly encounter the substrate after a specific amount of mixing which is adjusted in accordance with the nature of the desired coating. Usually, the time from which the calcium source and the replenished phosphate solution meet to the time for encountering the substrate will be less than about 1 sec., more usually less than about 10 msec. The final volume of the solution will generally be from about 2 to 30 times greater than the volume of the two solutions added, usually about 1 to 2 times greater.

The reactant solutions and the parent solution may be preheated or used at ambient temperature, generally being added at a temperature in a range of at least 20° C. to not more than about 90° C. The reaction may be maintained at a temperature of the range about 60°-90° C., preferably in the range of about 70°-85° C. The pH will be maintained in the range of about 5-8.5, more usually about 6-8, preferably about 6.5 to 7.5. The pH of the individual reactants and the parent solution may be individually adjusted to provide for specific crystal nucleation and crystal growth conditions.

The molar ratio of the solutions will generally have the calcium source at a molar ratio of 1- 2:1 to the phosphate source, more usually of about 1.5-2:1 to the phosphate source. The molarity of the most dilute concentration of the calcium source will generally be in the range of about 0.05 to 5M, more usually about 0.1 to 2.0M. The phosphate source will generally be from about 0.01 to 1.0M preferably about 0.05 to 0.5M. The more concentrated solution will generally range from about 2 to 10 times the least concentrated, more usually from about 2 to 8 times. The first reaction mixture solution, which provides for the high nucleation, will generally be at a concentration at least about 1.5 times the most dilute reaction mixture solution employed, more usually at least about 3 times, and not more than about 10 times, usually not more than about 7 times the most dilute reaction mixture solution. Particularly preferred is a series where the various solutions are 5 times, 3 times than the last and most dilute solution. The calcium and phosphate source will be added to provide a substantially stoichiometric ratio of the components of hydroxyapatite.

The calcium source may use any convenient counterion, depending on the purpose of the final product. Where the final product is to be introduced into a host, desirably only physiologically acceptable counterions will be employed. For the calcium salt, various organic and inorganic anions providing a water soluble source may be employed, such as acetate, succinate, nitrate, chloride, malonate, maleate tartrate, fumarate or other chelating anion. Of particular interest are carboxylates of 2 to 6, usually 2 to 4 carbon atoms. For phosphate, alkali metal or ammonium salts may be used, particularly sodium or ammonium. The choice of counterions and mixtures thereof will be determined to some degree on the interaction of the counterions, so as to avoid any precipitation or involvement of the counterions in the crystal structure.

The time for each coating will vary depending upon the particular substrate, the concentrations and conditions employed, and the like. Generally, each coating will take at least about 5 minutes, more usually at least about 30 minutes, and not more than about 12 hours, more usually not more than above 6 hours. Preferably, the time for the coatings are varied in a range from about 1 to 6 hours.

The substrates are introduced into the solution, where the substrate will preferably be down stream from the more proximal calcium source. Thus the phosphate source will preferably move downstream to combine with the calcium stream before encountering the substrate to be coated. Those areas not to be coated may be protected by a convenient protective coating or the coating may be removed from those areas which are not protected after completion of the process. Variations in concentration of the reactants can be achieved by either using more dilute solutions for addition of the reactants or by using different volumes and concentrations for the initial parent solution in which the substrate is immersed. Where the reactants are continuously added to the reaction mixture, after completion of the addition, the reaction may be allowed to continue, the additional time usually requiring from about 50 to 400%, usually from about 75% to 200%, of the total time for each individual layer formation.

After each coating the surface may be prepared by thorough cleaning to remove any surface contaminants for the next coating. Various methods for cleaning the substrate may be employed. After each coating, the samples may be removed and, carefully rinsed with an appropriate rinsing solution, e.g. deionized water. If desired, the sample may be dried and inspected by employing a volatile water miscible organic solvent, e.g., acetone, rinsing with the organic solvent, followed by air drying. After each individual coating, desirably the substrates are turned 180° to insure that the substrates are coated uniformly. When the coating has been completed, the samples are then inspected to insure uniformity, adhesion to the substrate, surface area enhancement, and for any other characteristic which may be appropriate.

The subject coatings may be combined with a wide variety of materials, such as collagen, bone growth factors, such as TGF-B, bone morphogenetic factor, combinations thereof, or the like. The growth factors may serve to enhance the growth of osteoblasts, while the growth factors and collagen may enlist bony ingrowth. These factors may be included in the reaction mixture or in a storage solution. Generally, the growth factors will be present in the solution in from about 1 $\mu$g/ml to 1 mg/ml. The coated devices can be shipped in aqueous media, where one or more factors may be present in the solution in which the coating is immersed. Alternatively, these factors may be freeze-dried on to the coated substrate to which they bind and then the device shipped dehydrated.

Various implant devices, for example, the femoral component of a total hip arthroplasty may be used where the devices may be composed of a wide variety of materials, particularly metals or hardened plastics, e.g. Co-Cr, Ti alloy steel, polyethylene, carbon fibre reinforced resins etc.

The following examples are offered by way of illustration and not be way of limitation.

EXPERIMENTAL

Protocol

Carefully cleaned samples are introduced into a 3 L insulated beaker comprising 25.05 g ammonium acetate in 250 ml of deionized water (dH$_2$O). The samples are downstream from a calcium acetate addition port and a rotating motorized stir propeller is centered and rotated at 60 rpm. The beaker is placed on a 9 inch heat/stir plate and the heat turned on to 8.0. The beaker is covered with a protective film to reduce evaporative heat loss. When the ammonium acetate solution has been heated to 75° C., the pH meter is turned on and the pH monitored, so that the solution is maintained at 80° C. and pH 7.4. Addition is then begun of the reactants at a rate to provide the desired stoichiometric ratio, where a solution 0.5M in calcium acetate and a second solution 0.3M in ammonium phosphate monobasic is continuously added, while maintaining the pH by the addition of concentrated ammonium hydroxide. The addition is carried out over a period of two hours, at which time stirring and heating is then continued for an additional two hours to provide a total period of about four hours.

The sample substrate may then be removed, washed, dried by washing with acetone and allowed to air dry, if the substrate is to be inspected between coatings.

The above procedure is repeated, except the solutions employed have 60% of the original concentration. A third coating may then be employed where the reactant solutions have 20% of the original concentration.

When the coatings are finished, the coatings are inspected by rubbing with a bare finger or glove to determine whether the coating comes off and by placing a piece of VWR lab tape on the surface and pulling the tape off. If in either case, significant bare metal is exposed, the coating may be removed and the process repeated.

The general procedure described above was followed with six Vitallium porous-implant rods from Howmedica Inc. (Rutherford, N.J.) The system was set up as described and the coating begun when the temperature reached 80.0° C. and the solution was at pH 7.4. The run required four hours during which time the temperature varied from about 79° to 84° C. and the pH from about 7.39 to 7.43. About 160 ml of conc. ammonium hydroxide was used to maintain the PH. After about 20 min., polyethylene balls were added to minimize evaporation. The rods were turned after about 30 min. and one hour, while the rods were moved in a clockwise direction at about 95 min. and the beaker moved to maintain the spatial relationship between the rods and the reagent sources. Addition of reagents was completed at about 115 min.

Devices comprising Co-Cr beaded rod (Howmedica PCAT TM surface) were prepared as described above for transmetaphyseal femur implants, with a 1 mm radial gap in fifteen dogs.

The protocol provides for the evaluation for safety and effectiveness of a bioceramic coating applied to a Vitallium porous-coated implant. Further, it also tests the ability of the coating to bridge a clinically relevant 1 mm bone-implant gap. The study uses the dog as an animal model. The non-weight bearing model has implants placed across each femoral condyle with a 1 mm gap maintained throughout the cancellous region of the condyle. One femur has the coated implant inserted. The contralateral femur has the uncoated plug implanted and serves as a control. This model allows the mechanical and histologic evaluation of the bone-implant interface.

The purpose of the non-weight bearing study is to show the effectiveness of the applied bioceramic coating to the implant surface. Effectiveness is evidenced by a significantly increased push-out strength as compared to the non-coated implant. Additionally, the safety of the coating on the non-weight bearing implant and the osteoconductive ability of the bioceramic coating can be assessed by histopathologic evaluation of the implant site.

Experimental Design

A porous-coated vitallium plug is surgically implanted transcondylarly into the distal femur of 15 adult dogs. The plugs are placed bilaterally, one femur has a plug coated with the bioceramic material while the contralateral femur has a non-bioceramic coated plug implanted. The bone-implant interface is evaluated mechanically to quantify the shear force required to initially dislodge the implant. On representative paired specimens, undecalcified histology is performed to determine the mode of interface failure and skeletal reaction to the bioceramic coating.

The 15 dogs are divided into 3 groups. Groups I, II, and III each has 5 subjects. The respective sacrifice times following implantation of the coated and uncoated plugs are 3, 6, and 12 weeks.

Experimental Subjects

Skeletally mature, heartworm-free dogs are used as experimental subjects. The animals are examined for any evidence of disease. Skeletal maturity and the absence of previous or current skeletal pathology is confirmed radiographically. The minimum body weight is approximately 20 kilograins.

The breed and sex of the dogs used is dependent on laboratory animal availability. Where possible, purpose-bred subjects of known ages are used. If purpose-bred animals are used, the dogs do not vary by more than one year in ages.

Animal Housing

The subjects are conditioned for an appropriate period of time. Following quarantine, the animals are maintained in runs, either individually or in pairs, depending on the cage size. Animal housing conditions conform with the applicable laws and regulations relating to laboratory animals, i.e., Animal Welfare Act, Public Law 89-544 as amended in Public Law 99-198, Federal Register 52:61, United States Department of Agriculture—Animal and Plant Health Inspection Service (USDS-APHIS), 1985 and Public Health Service Policy on Humane Care of Laboratory Animals, office for Protection Against Research Risks/National Institutes of Health (OPRR/NIH), September, 1986.

Implant Description

The porous-coated Vitallium implants have two different surface conditions. These are the bioceramic coated and uncoated surfaces. The dimensions of the implants are approximately 6.4 mm in diameter and either 25 mm or 30 mm in length. Both ends are cut straight to allow attachment of an 8.4 mm diameter by 3 mm thick teflon washer. Two washers, one on each end of the plug are attached.

All of the implants are supplied by Howmedica. They are sterilized in individual packages with a pair of teflon washers included.

Surgical Technique

The surgical implantation technique is identical for both rearlimbs. All surgeries are done under strict asepsis. Peri-operative antibiotics and pre-anesthetic medication is dosed at he discretion of the surgeon. Anesthesia is induced with an ultra-short acting barbiturate followed by endotracheal intubation. The subject is maintained with a balanced mixture of oxygen and an inhalatory anesthetic agent.

The surgical approach is as follows. A curved, lateral skin incision is made from the distal one-third of the femur to the level of the tibial plateau. The skin is bluntly dissected and retracted to allow a lateral parapatellar approach into the stifle joint. An incision is made parallel to the lateral border of the patella and patellar ligament. This extends from the lateral side of the fascia lata along the cranial border of the biceps femoris and into the lateral fascia of the stifle joint.

The biceps femoris and attached lateral fascia are retracted allowing an incision into the joint capsule. The joint is extended and the patella luxated medially exposing the femoral condyles.

The desired point of drilling is from the middle of the lateral to medial condyles, midway between the fabella and the most cranial part of the trochlear ridge. The lateral fabella are identified with a sterile needle to assist in determining the point of drilling. A pilot drill hole is placed once the alignment has been verified. The depth across the condyles is measured with a depth gauge in order to determine if the 25 Mm or 30 Mm long implant should be used. After the desired implant is chosen the hole is sequentially enlarged until an 8.4 mm drill hole is achieved. The periosteum around the lateral drill hole is reflected to prevent being pulled in during insertion of the implant. The drill hole is flushed from the lateral to medial direction with sterile saline.

The plug and lateral washer assembly is placed into the hole from the lateral side. The medial washer is then attached to the opposite end of the plug. An equal amount of the implant should protrude from the lateral and medial border of the condyles. Routine closure of the joint is accomplished in three or four layers using appropriate suture material.

The distribution of implants for each dog in the three groups is described in the following Table reporting the results:

Post-Operative Period

If possible, following the completion of surgery, with the animal still anesthetized, postoperative radiographs are made. Two views are taken, the lateral to medial and the craniocaudal view. Care is taken to assure the views are parallel to the plane of the implant. At this time, the anesthetic gas is turned off and oxygen flow maintained for five minutes. The subject is returned to the prep room after the radiographs are taken. A modified Robert-Jones bandage is applied to each hindlimb. The endotracheal tube is pulled once the subject displays a swallowing reflex. Following removal of the endotracheal tube, the dog is moved to a cage to recover. Post-operative analgesics are given if the animal displays any signs of distress or discomfort.

The day after surgery, if the animal is able to walk, it is returned to the housing quarters. The bandages are checked daily. After 2-5 days, the bandages are removed. New bandages may be put on, as appropriate. Skin sutures, if present are removed 10-14 days post-op. All animals are examined daily for signs of pain or infection. Appropriate measures are taken if either occurs.

The subjects are housed for either 3, 6, or 12 weeks after implantation. During this time, normal activity is allowed. Radiographs are made at the time of sacrifice. As before, two views, the lateral to medial and the craniocaudal, are taken. The positioning is the same as the previous films.

Fluorochrome Bone Labels

Oxytetracycline is given at a single dose of 30-35 mg/kg intravenously. This is generally done 3 days prior to sacrifice.

Euthanasia

The subjects are euthanatized at the end of the study in a humane manner according to the guidelines set forth by the AVMA Panel on Euthanasia (JAVMA, January, 1986).

Specimen Collection and Handling

Immediately following sacrifice, the rearlimbs are disarticulated at the coxofemoral and patellofemoral joints. All soft tissues are removed. Popliteal and inguinal lymph nodes are isolated and fixed in formalin for later evaluation. The paired femurs are labeled and frozen.

For shipping for evaluation, the specimens are frozen in dry ice.

Mechanical Testing and Histology

To mechanically evaluate the bone-implant interface strength, a push-out test is conducted. Each femoral condyle is sectioned through the lateral and medial cortical wall of each condyle on the inner surfaces of the teflon washers, orthogonal to the plane of the implant, with a low deformation wire saw. The direction of applied force is from medial to lateral, opposite to the direction of insertion. The cross-head speed of the testing machine is 0.5 mm per minute. The testing is stopped when the force to push-out the implant begins to decline.

The tested specimens are sequentially dehydrated in increasing concentrations of ethanol. They are embedded in methacrylate, sectioned either sagittal or orthogonal to the implant, and microradiographs taken. This is followed by grinding to a desired thickness and differential staining. The prepared sections are evaluated with light and ultraviolet microscopy to determine the mode of bone-implant failure and to assess the skeletal reaction to the uncoated and coated surfaces.

The following table provides the results of the test with the porous-coated Vitalluim plug coated in accordance with the subject invention as described above.

| ANIMAL STUDY | | | |
|---|---|---|---|
| Animal Number | Group (week) | Coated (MPa) | Uncoated (MPa) |
| 1201 | 3 | 0.82 | 0.21 |
| 1203 | 3 | 0.60 | 0.24 |
| 1774 | 3 | 1.19 | 0.39 |
| 1769 | 3 | 0.10 | 0.03 |
| 1771 | 3 | 0.55 | 0.14 |
| mean ± sd | | 0.65 ± 0.36 | 0.20 ± 0.12 |
| 1208 | 6 | 1.75 | 0.35 |
| 1205 | 6 | 0.72 | 0.51 |
| 1210 | 6 | 0.79 | 0.20 |
| 1537 | 6 | 1.90 | 0.25 |
| mean ± sd | | 1.29 ± 0.61 | 0.33 ± 0.13 |
| 1206 | 12 | 3.11 | 0.83 |
| 1200 | 12 | 3.16 | 0.40 |
| 1278 | 12 | 2.61 | 0.31 |
| 1202 | 12 | 1.31 | 0.65 |
| 1535 | 12 | 3.28 | 0.87 |
| mean ± sd | | 2.69 ± 0.73 | 0.61 ± 0.22 |

| STATISTICAL ANALYSIS Student's Paired T-Test | | |
|---|---|---|
| • | 3 week group n = 5 | $0.05 < p < 0.02$ |
| • | 6 week group n = 4 | $0.10 < p < 0.05$ |
| • | 12 week group n = 5 | $0.01 < p < 0.001$ |

Histomorphometry also shows that the subject coating results in the gap being filled and, statistically decreases the time in which the gap is filled. The subject coatings are biomechanically competent.

It is evident from the above results, that the subject method provides for strongly adherent coatings, which do not fracture readily and promote for ingrowth of natural bone. The method provides for the coating of all surfaces, even hidden surfaces, which is a distinct advantage as compared to other techniques for coating porous portions of prostheses. In addition, the surfaces allow for binding of a wide variety of proteins, and can be shipped in a state which maintains in solution various additives, which may aid in the interaction with native bone and the prosthesis. The coating procedure is substantially reproducible, allowing for uniformity and homogeneity of the coating composition. Bonding to the substrate is found to be strong, so that the coated substrate may be subjected to reasonable abrasion and handling without affecting the coating. This subject calcium phosphate coating foster rapid bony ingrowth due to its high peptide-binding surface area which stimulates osteogenesis. The subject compositions for a bone growth factor delivery surface coating.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An hydroxyapatite coated substrate prepared according to the method comprising:
   contacting a solid substrate with a solution comprising soluble calcium ion and soluble phosphate ion at a first concentration providing for small crystal formation and a high density of nucleation sites forming a first coating on said solid substrate, wherein said calcium ion is at a molar ratio to said phosphate ion of about 1-2:1, and said solid substrate is a metal or hardened plastic;
   contacting said solid substrate with said small crystal coating with a solution comprising soluble calcium ion and soluble phosphate ion at a second concentration lower than said first concentration providing for a larger crystal formation and a lower density of nucleation sites forming a coating over said first coating, wherein the molarity of the calcium ion is in the range of about 0.05-5M, the molarity of the phosphate ion is in the range of about 0.01-1M, and the concentration of the calcium and phosphate ions in said solution is at least 1.5-fold lower than said first concentration;
   wherein the pH of each of said solutions is in the range of 5-8.5 and the temperature is in the range of 60°-90° C.; and,
   removing said solid substrate from solution.

2. An hydroxyapatite coated substrate prepared according to the method comprising:
   contacting a solid substrate with a solution comprising soluble calcium ion and soluble phosphate ion at a first concentration providing for small crystal formation and a high density of nucleation sites forming a first coating on said solid substrate, wherein said calcium ion is at a molar ratio to said phosphate ion of about 1-2:1, and said solid substrate is a metal or hardened plastic;
   contacting said solid substrate with said small crystal coating with a solution comprising soluble calcium ion and soluble phosphate ion at a second concentration lower than said first concentration providing for a larger crystal formation and a lower density of nucleation sites forming a coating over said first coating, wherein the molarity of the calcium ion is in the range of about 0.05-5M, the molarity of the phosphate ion is in the range of about 0.01-1M, and the concentration of the calcium and phosphate ions in said solution is at least 1.5-fold lower than said first concentration;
   wherein the pH of each of said solutions is in the range of 5-8.5 and the temperature is in the range of 60°-90° C.; and,
   removing said solid substrate from solution, comprising a bone growth activating amount of a growth factor for osteoclasts or collagen.

3. An hydroxyapatite coated substrate prepared according to the method comprising:
   contacting a solid substrate with a solution stream comprising soluble calcium ion and soluble phosphate ion at a temperature in the range of 60-90 degrees C., a pH in the range of about 5-8.5 and at a first concentration, providing for small crystal formation forming a first coating on said solid substrate, wherein said calcium ion is at a molar ratio to said phosphate ion of about 1-2:1, and said solid substrate is a metal or hardened plastic and said calcium ion is introduced into said stream proximal to said solid substrate and said phosphate ion is introduced into said stream distal to said solid substrate;
   repeating said contacting of said solid substrate with said small crystal coating at least once with a solution comprising soluble calcium ion at a molarity in the range of about 0.05-5M and soluble phosphate ion at a molarity in the range of about 0.01-1M and at a temperature in the range of 60-90 degrees C. a pH in the range of about 5-8.5 and at a second concentration at least two-fold lower than said first concentration providing for larger crystal formation forming a coating over said first coating; and
   removing said solid substrate from solution.

4. An hydroxyapatite coated substrate prepared according to the method comprising:
   contacting a solid substrate with a solution stream comprising soluble calcium ion and soluble phosphate ion at a temperature in the range of 60-90 degrees C., a pH in the range of about 5-8.5 and at a first concentration, providing for small crystal formation forming a first coating on said solid substrate, wherein said calcium ion is at a molar ratio to said phosphate ion of about 1-2:1, and said solid substrate is a metal or hardened plastic and said calcium ion is introduced into said stream proximal to said solid substrate and said phosphate ion is introduced into said stream distal to said solid substrate;
   repeating said contacting of said solid substrate with said small crystal coating at least once with a solution comprising soluble calcium ion at a molarity in the range of about 0.05-5M and soluble phosphate ion at a molarity in the range of about 0.01-1M and at a temperature in the range of 60-90 degrees C. a pH in the range of about 5-8.5 and at a second concentration at least two-fold lower than said first concentration providing for larger crystal formation forming a coating over said first coating; and
   removing said solid substrate from solution, comprising a bone growth activating amount of a growth factor for osteoclasts or collagen.

5. A substrate according to claims 1 or 3, wherein said substrate is porous.

6. A substrate according to claims 1 or 3, wherein said substrate is comprised of metal or hardened plastic.

7. A substrate according to claim 6, wherein said substrate is a prosthesis device comprised of Co-Cr or Ti/alloy.

8. A substrate according to claims 2 or 4, wherein said coated substrate is hydrated.

9. A substrate according to claims 2 or 4, wherein said coated substrate is freeze dried.

10. A substrate according to claims 2 or 4, wherein said coated substrate comprises a bone growth factor.

11. A substrate according to claims 2 or 4, wherein said coated substrate comprises collagen.

12. A substrate according to claims 2 or 4, wherein said coated substrate comprises an antibiotic.